(12) United States Patent
Haidl et al.

(10) Patent No.: US 7,083,279 B2
(45) Date of Patent: Aug. 1, 2006

(54) PROCESS AND AN APPARATUS FOR MAKING PLASTIC MATERIAL SPECTACLE LENSES

(75) Inventors: Markus Haidl, Aalen (DE); Michael Mertin, Aalen (DE); Michael Zaiser, Boebingen (DE)

(73) Assignee: Carl Zeiss Vision GmbH, Aalen (DE)

( * ) Notice: Subject to any disclaimer, the term of this patent is extended or adjusted under 35 U.S.C. 154(b) by 0 days.

(21) Appl. No.: 11/052,210

(22) Filed: Feb. 7, 2005

(65) Prior Publication Data

US 2005/0189664 A1    Sep. 1, 2005

Related U.S. Application Data

(63) Continuation of application No. PCT/EP03/07075, filed on Jul. 2, 2003.

(30) Foreign Application Priority Data

Aug. 7, 2002  (DE)  ............................. 102 36 713

(51) Int. Cl.
*G02C 7/02*      (2006.01)
(52) U.S. Cl. ..................................... 351/177
(58) Field of Classification Search ................ 351/177, 351/246
See application file for complete search history.

(56) References Cited

U.S. PATENT DOCUMENTS 4,781,452 A * 11/1988 Ace ........................... 351/177
6,637,880 B1 * 10/2003 Yamakaji et al. ........... 351/177
6,871,955 B1 * 3/2005 Yamakaji et al. ........... 351/169

FOREIGN PATENT DOCUMENTS

| EP | 0 092 364 A1 | 10/1983 |
| EP | 0 299 690 A2 | 1/1989 |
| EP | 0 576 268 A1 | 12/1993 |

* cited by examiner

*Primary Examiner*—Jordan M. Schwartz
(74) *Attorney, Agent, or Firm*—Harness, Dickey & Pierce P.L.C.

(57) ABSTRACT

A process and an apparatus are used for making spectacle lenses from plastic material. The spectacle lenses are worked by working plastic material blanks as a function of data representing the surface of the finished spectacle lens as well as work process parameters. The plastic material blanks are worked in one of a plurality of de-centralized units. For individualized spectacle lenses the data are computed in a central unit as first data and are transmitted to the decentralized unit, and for non-individualized spectacle lenses the data are read out of a first memory in the decentralized unit.

24 Claims, 1 Drawing Sheet

PROCESS AND AN APPARATUS FOR MAKING PLASTIC MATERIAL SPECTACLE LENSES

CROSS-REFERENCE TO RELATED APPLICATIONS

This application is a continuation of international patent application PCT/EP2003/007075, filed Jul. 2, 2003 and designating the U.S., which was not published under PCT Article 21(2) in English, and claims priority of German patent application DE 102 36 713.2, filed Aug. 7, 2002, which is incorporated herein by reference.

FIELD OF THE INVENTION

The invention, generally, relates to the field of making spectacle lenses from a plastic material.

More specifically, the invention relates to a process for making plastic material spectacle lenses, wherein the spectacle lenses are worked by working plastic material blanks as a function of data representing the surface of the finished spectacle lens as well as work process parameters.

The invention, further, relates to an apparatus for making plastic material spectacle lenses, comprising a working installation for plastic material blanks, and a computer for controlling the working installation as a function of data representing the surface of the finished spectacle lens as well as parameters of the work process.

BACKGROUND OF THE INVENTION

Processes and apparatuses of the afore-mentioned type are generally known.

In the field of modern spectacle lenses, in particular progressive power lenses, one distinguishes between so-called "non-individualized" and "individualized" lenses.

Non-individualized progressive power lenses are lenses which are conventionally standardized and, if made from a plastic material, are made as semi-finished products in a molding process. The semi-finished products are either made at one of the big established spectacle lens manufacturers, or are made within a de-centralized system at a specialized wholesaler who not only manufactures the blanks but also effects the surface working according to patient's data that he obtains from optician's shops.

Conventionally the semi-finished products are manufactured in a variety of models which distinguish with respect to their base curve, their addition power, and their right/left assignment as well as their type of glass. The spectacle lens is then made from the respective appropriate blank according to the needs of the particular patient.

In the field of individualized progressive power lenses several additional parameters, as compared to a non-individualized progressive power lens, are determined by the ophthalmologist or the optician, wherein these additional parameters enter into the computation of the lens. Each individualized progressive power lens is, therefore, individually computed and made for a specific patient.

Therefore, individualized progressive power lenses at this time may only be made by a few manufacturers, because besides the necessary manufacturing technology, the know-how for computing such individualized progressive power lenses must also be at hand. These manufacturers are normally only the experienced spectacle lens manufacturers.

In the case of non-individualized progressive power lenses, the plastic material blank or the semi-finished product, resp., is provided with a finished and predetermined progressive power surface, normally on its front surface. The working on the semi-finished product, individual for the respective patient, in contrast, takes place only on the rear surface (the so-called "prescription surface").

For individualized progressive power lenses this approach cannot be used because in that case besides working the rear surface individually for the patient, also the front surface has to be worked for making an individual progressive power surface for the patient.

Seen together, this means that for individualized progressive power lenses according to today's state of the art, the manufacture may only take place at the big spectacle lens manufacturers which, however, is an obstacle for a wider distribution of such spectacle lenses that would be in the interest of patients. This is because a longer period of time is needed for making such individualized progressive power lenses, that customers' complaints are more complicated to handle and that a sufficient competition may not always be guaranteed.

Document EP 0 576 268 B1 describes a system for making spectacles. The system consists of a plurality of regionally distributed sales outlets that are connected to a central manufacturing plant via a public communication network. Data relating to the respective spectacle as well as data relating to the spectacle lenses are entered into a data acquisition device and are transmitted to the central manufacturing plant. No manufacturing installations whatsoever are provided in the sales outlets.

Document EP 0 299 690 A2 describes a system for processing prescriptions for contact lenses. The system consists of a plurality of regionally distributed terminals located at ophthalmologists' offices. The terminals, e.g. personal computers or telephones, are connected to a central computer via a public communication network. Accordingly, orders are handled, prescriptions are stored, patients' files are administrated etc. Also in this case, no manufacturing takes place in the area of the terminals.

A similar system for the distribution of spectacles and spectacle lenses is described in document U.S. 2001/0042028, which distinguishes between registered and not yet registered patients.

Document EP 0 092 364 A1 describes an apparatus for working the rim of a spectacle lens such that it will fit into a given non-circular spectacle frame. The data relating to the spectacle frame are stored in an electronic memory or, in the event of a new frame, are measured and then stored in the memory, resp. These data are fed to a rim working installation.

It is, therefore, an object underlying the present invention to improve a process and an apparatus of the type specified at the outset such that the making of conventional, non-individualized progressive power lenses as well as specifically the making of individualized progressive power lenses is not only possible at a few spectacle lens manufacturers, but also within a de-centralized system at wholesale companies, large laboratories and the like, as are today active in many markets.

SUMMARY OF THE INVENTION

As used herein and in the accompanying claims:
i) "central unit" and "centralized unit" refer to a central computer or central processing unit;
ii) "de-centralized unit" refers to a processing or working installation that is physically remote from the location of the central or centralized unit;

iii) "non-individualized spectacle lenses" refers to spectacle lenses having both surfaces standardized, or so-called "off-the-shelf" lenses; and iv) "individualized spectacle lenses" refers to spectacle lenses having one or both surfaces that are worked based upon data specialized to a particular individual, or so-called custom lenses.

According to a process as mentioned at the outset, this object is achieved in that the plastic material blanks are worked in one of a plurality of de-centralized units, that either for individualized spectacle lenses the data are computed in a central unit as first data and are transmitted to the decentralized unit, or for non-individualized spectacle lenses the data are read out of a first memory in the decentralized unit.

According to an apparatus as mentioned at the outset, the object is further achieved in that a central unit as well as a plurality of de-centralized units are provided, wherein the de-centralized units are connected to the central unit by a line network, wherein, further, the central unit has a computing stage for computing first data for individualized spectacle lenses, and memories for second data for non-individualized spectacle lenses are provided in the de-centralized units, and that the computer has means for controlling the working installation either as a function of the first or of the second data.

The object underlying the invention is thus entirely solved.

According to the invention, the working of conventional non-individualized progressive power lenses is enabled with the facilities of the respective de-centralized unit alone which has stored the required sets of data for the specific surface shape and the required work parameters such that for the manufacture within the de-centralized units these sets of data may be directly accessed. If, on the other hand, an individualized progressive power lens shall be made, one may go back to the computing capabilities within the central unit so that these capabilities must not be held available within each and every de-centralized unit.

The invention, therefore, makes it possible for the first time to distribute the competence of making individualized progressive power lenses onto a de-centralized level with many wholesalers and laboratories acting on the same market, such that the processing time is reduced and an efficient competition takes place.

In preferred embodiments of the invention, the plastic material blanks are first molded and then worked, as known per se. The working is preferably effected by lathing, by grinding, by milling or other known work processes.

As already mentioned, depending on the kind of lens to be made, one of the surfaces of the plastic material blank may be made as a finished surface already during molding and only the other surface is worked thereafter, whereas, as an alternative, also none of the surfaces of the plastic material blank may be made as a finished surface during molding and both surfaces are worked thereafter.

In the first-mentioned case, the one surface is preferably configured as a pre-fabricated progressive power surface and the other surface is worked as a prescription surface. As an alternative, however, the one surface may be configured in coarse steps as a spheric or as a toric surface and the other surface may be worked as a combined progressive power and prescription surface. Preferably the other surface in both cases is on the rear side of the spectacle lens.

In the last-mentioned case it is even possible to manufacture the plastic material blanks outside the de-centralized units as unworked raw blanks, the so-called "Hockey Pucks" which are then supplied to the de-centralized units. This results in substantial cost savings.

Further, it is preferred when in an also known manner the plastic material blanks are first worked by chip-cutting, are then polished and are finally marked.

In preferred improvements of the inventive process, the first and the second data, resp., are computed and read-out, resp., as a function of input signals, entered to the de-centralized unit.

These measures have the advantage that an incoming order for a specific spectacle lens may be immediately entered into a computer within the de-centralized unit, e.g. via a keyboard, and that required data may directly be computed or read-out from the entered signals. This likewise contributes to a reduction of the entire processing time for such an order.

In variations of this embodiment, it is preferred when after the input signals have been entered, a work piece carrier is first selected within the de-centralized unit, that the work piece carrier is then provided with a plastic material blank to be worked and that the work piece carrier is then fed to a working installation.

This holds true in particular when a marking on the work piece carrier is read out and is then linked with the input signals to a set of data.

This measure has the advantage that orders may be controlled reproducibly and that the data of the order and of the processing may be stored for documentation purposes.

For that purpose, the second data read out from the first memory as a function of the input signals are added to the set of data, wherein, preferably, the set of data is transmitted to the central unit and is stored therein.

When doing so, an entirely controlled and documented work operation is generated which guarantees a high working quality at low waste.

There are particularly preferred embodiments of the invention in which the central unit has a second memory for storing updates for the second data, wherein prior to the reading-out of second data from the second memory, the second data are compared with the updates. Insofar, it is particularly preferred when the second data in the first memory are replaced by the updates if the second data are not in accordance with the updates.

These measures have the advantage that also during the making of conventional non-individualized progressive power lenses, one may at any time go back to the latest sets of data from the manufacturer, when at the occasion of a new order or according to another raster the central unit is interrogated as to whether the sets of data as are stored in the de-centralized units, are still the actual data or not. A quick electronic update in such situations ensures that the end-user and, hence, the patient has always the latest data available at any time.

Further advantages will become apparent from the description and the appended drawing.

BRIEF DESCRIPTION OF THE DRAWING

An embodiment of the invention is shown in the drawing and will be described in further detail in the subsequent description.

DETAILED DESCRIPTION OF THE PREFERRED EMBODIMENTS

Figure 1:
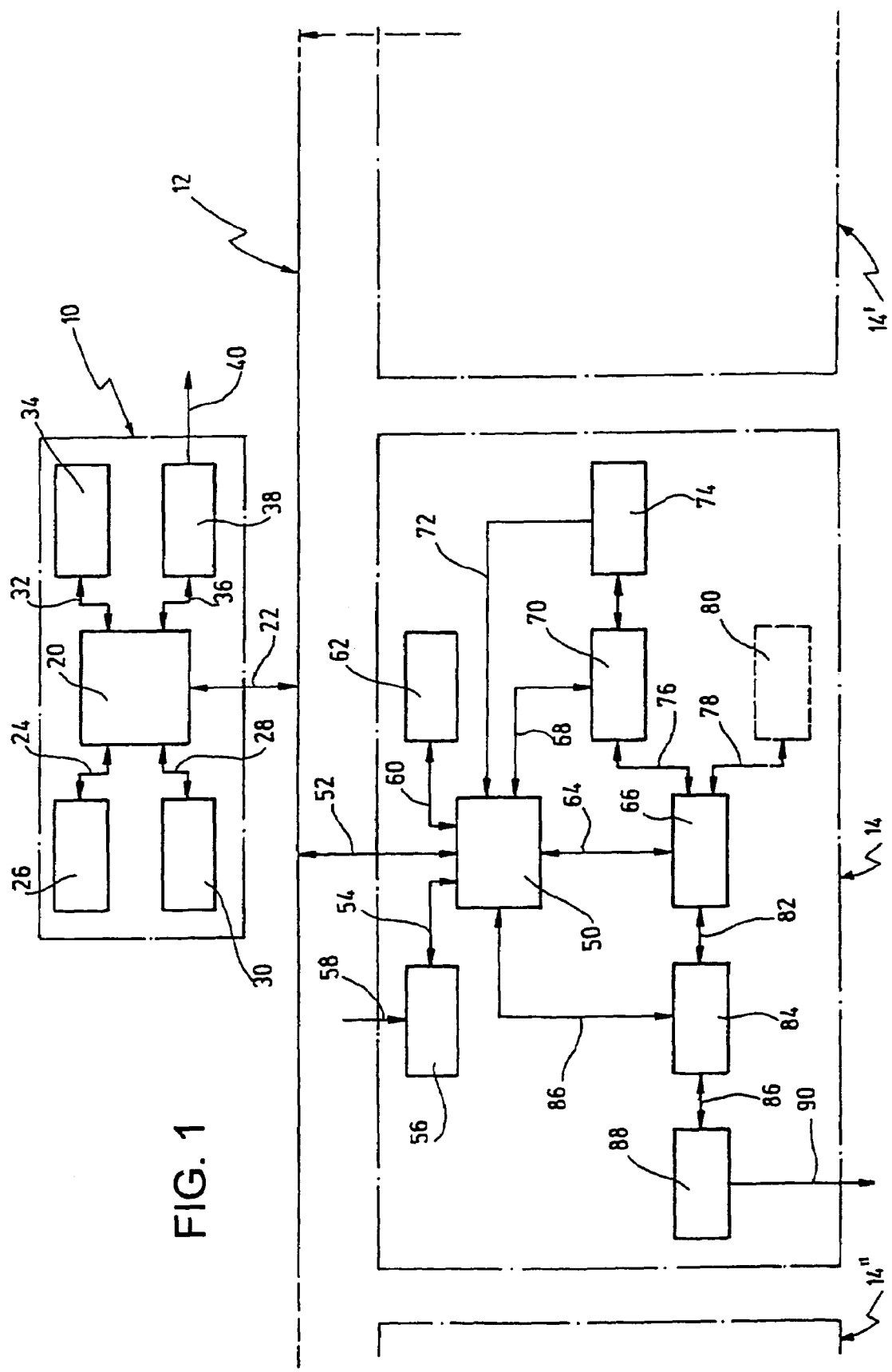
FIG. 1 illustrates a schematic block diagram of an embodiment of the inventive process or the inventive apparatus.

In the figure, reference numeral 10 indicates a central unit as a whole. Central unit 10 performs the function of a server. Central unit 10 is connected to a line network 12. The line network 12 may be a conventional line network as it is commonly used for transmitting data or other signals, however, line network 12 may also be the Internet.

De-centralized units having the function of a client are likewise connected to line network 12. In the FIGURE only one such unit is shown at 14 in detail, whereas further units 14', 14" are only schematically indicated. It goes without saying that the number of de-centralized units 14, 14', 14" is by no means limited, nor is it limited with respect to its regional distribution.

Central unit 10 comprises a first computer 20. Computer 20 is connected to line network 12 via a line 22. When the term "line" is used hereinafter, it is to be understood to mean any kind of interaction between two assemblies or installations which serves to transmit data or also to hand-over goods. It goes, further, without saying that the block diagram of the FIGURE that will be described hereinafter may only be understood as an example in its particularly given configuration and that many of the functions that will be described hereinafter may also be configured as parts of a programmed control without being limited by certain apparatus configurations.

First computer 20, further, is connected to a computing stage 26 via a line 24. Computing stage 26 computes sets of data for individualized progressive power lenses according to values given for an individual patient. These sets of data comprise the corresponding surface shape for the two faces of the spectacle lens as well as the work parameters resulting therefrom which are required for the working of a plastic material blank in order to achieve the computed surfaces. Insofar, the term "data" is to be understood to mean any combination of information that is needed for making a certain surface of a spectacle lens.

Further, a first memory 30 is connected to first computer 20 via a line 28. First memory 30 has stored therein updates for non-individual progressive power lenses as will be explained below.

A line 32 interconnects first computer 20 with a second memory 34 having stored and, hence, documented therein order-related data.

Finally, a line 36 connects first computer 20 to a computing stage 38 which, by means of an appropriate word processing, is responsible for correspondence and billing, as indicated by an arrow 40 pointing outwardly.

De-centralized unit 14 comprises a second computer 50 being connected to line network 12 via a line 52 in the manner already described. Another line 54 connects second computer 50 with a terminal 56, which, for example, may be controlled by a keyboard 58, a mouse, a data line or the like. The functions of terminal 56 may also be integrated into second computer 50. Terminal 56 is used for entering patient-specific data as are required for the making of a desired spectacle lens.

A line 60 connects second computer 50 with a third memory 62 having stored therein data for the determination of surface and process parameters for non-individualized progressive power lenses.

By means of a line 64, second computer 50 is connected to a work piece carrier 66. Moreover a line 68 connects second computer 50 with a molding machine 70 in which the plastic material blanks are molded. For doing so the required shaping elements for the molding machine 70 may be brought from a molding shell stock 74, the stock 74 being controlled by second computer 50 via a line 72. The plastic material blanks manufactured within molding machine 70 are transferred to work piece carrier 66 via a line 76.

As an alternative to the afore-described molding process by means of a molding machine, the de-centralized unit 14 may also use externally prefabricated raw blanks, the so-called "Hockey Pucks" which are held available in a corresponding stock 80 and are adapted to be transferred to the work piece carrier 66 via a line 78.

The work piece carriers are fed to a working installation via a line 82. Working installation, in turn, is adapted to be controlled by second computer 50 via a line 86. The plastic material blanks are worked within working installation 84 by lathing, grinding, milling and the like, and are preferably also polished and, finally, marked.

The finished plastic material spectacle lenses then leave working installation 84 via a line 86 and then come into a dispatch unit 88 from where they are delivered as indicated with an arrow 90 pointing outwardly.

Now, two examples for the operation during the making of a plastic material spectacle lens shall be explained:

A specific order is based on patient-specific data which are preferably entered into terminal 56 manually via keyboard 58. Second computer 50 now determines whether the desired spectacle lens is an individualized or a non-individualized lens.

In the first case, a connection is made to central unit 10 via line network 12. The individual data for the order being processed are now computed within computing stage 26, i.e. the surfaces to be generated, including the required data for the process parameters of the respective work operation. These data are transmitted to the de-centralized unit 14 via line network 12. Simultaneously the data that have thus been determined, are transferred into the archives of second memory 34.

Second computer 50 now initiates the work operation with the data that have just been transmitted. For that purpose, either a plastic material blank is molded within de-centralized unit 14 by means of molding machine 70 and molding shell stock 74, or, considering that both surfaces of the plastic material blank have to be worked anyway, an entirely unworked raw blank is taken from puck stock 80.

Work piece carrier 66 is now equipped with the blank provided by the one or the other method. Work piece carrier 66 bears a mark that is read and transmitted to second computer 50 in order to be able to document the respective manufacturing operation also insofar. Work piece carrier 66 together with the blank now comes into working installation 84 where the individualized progressive power lens is made as described at the outset by working the front surface and the rear surface. Preferably the lens is then polished at the front or at the rear surface and, finally, it is also marked.

It is also possible to work only one of the two surfaces, preferably the rear surface. Moreover, it is possible for individualized progressive power lenses to provide the progressive power surface together with the prescription surface on the same side, preferably on the rear side, of the spectacle lens. In that case one would start for the working from a semi-finished product in which the surface that shall not be worked is already finished. For that purpose a spheric or a toric surface, each in coarse steps, would normally be sufficient.

After having left working installation 84, the finished spectacle lens is preferably provided with a surface finish, like, for example, a hardening coating and/or a an antireflection coating and/or an hydrophobic coating. The coating installations may also be connected to second computer 50. A non-interleaved operation is, however, also possible.

The spectacle lens having been made as described is now transferred to the dispatch department.

The data collected during the manufacturing process are transmitted from second computer to central unit 10 via line network 12. The data are likewise entered into the archives of second memory 34 and are processed in computing stage 38 for the subsequent correspondence with the customer.

In the case of a non-individualized lens, the process develops differently insofar as second computer 50 takes the data that are required for the work directly from third memory 62 which is also located in de-centralized unit 14. Preferably, prior to adopting the work data from third memory 62, an update is made in that second computer 50 makes a connection with central unit 10 via line network 12 for checking within first memory 30 whether the data read from third memory 62 correspond to the latest state of the art for the particular non-individualized progressive power lens. If a comparison shows that third memory 62 still has out-of-date data stored therein, these data are first updated by an exchange from first memory 30 and the updated data are used for the subsequent working operation.

The working now takes place in the same manner as has been described above for the case of individualized progressive power lenses.

The invention claimed is:

1. A process for making plastic material spectacle lenses, wherein said spectacle lenses are worked by working at least one of two surfaces of plastic material blanks as a function of data representing a surface of said spectacle lens in a finished state as well as work process parameters, wherein said plastic material blanks are worked on at least one surface thereof in one of a plurality of de-centralized units, wherein, further, for individualized spectacle lenses said data are computed in a central unit as first data and are transmitted to said decentralized unit, whereas for non-individualized spectacle lenses said data are read out as second data from a first memory in said decentralized unit.

2. The process of claim 1, wherein said plastic material blanks are first molded and then worked.

3. The process of claim 2, wherein said plastic material blanks are worked by lathing.

4. The process of claim 2, wherein said plastic material blanks are worked by grinding.

5. The process of claim 2, wherein said plastic material blanks are worked by milling.

6. The process of claim 2, wherein a first of said surfaces of said plastic material blank is made as a finished surface during molding, whereas only a second of said surfaces is worked.

7. The process of claim 6, wherein said first surface is configured as a prefabricated progressive power lens and said second surface is worked as a prescription surface.

8. The process of claim 7, wherein said second surface is on the rear side of the spectacle lens.

9. The process of claim 6, wherein said first surface is configured as a spheric surface, and said second surface is worked as a combined progressive power and prescription surface.

10. The process of claim 9, wherein said second surface is on the rear side of the spectacle lens.

11. The process of claim 6, wherein said first surface is configured as a toric surface, and said second surface is worked as a combined progressive power and prescription surface.

12. The process of claim 11, wherein said second surface is on the rear side of the spectacle lens.

13. The process of claim 2, wherein none of said surfaces is made as a finished surface during molding and both surfaces are worked.

14. The process of claim 13, wherein said plastic material blanks are manufactured outside said de-centralized unit as non-worked raw parts and are then fed to said de-centralized unit.

15. The process of claim 1, wherein said plastic material blanks are first worked by chip-cutting, are then polished and are finally marked.

16. The process of claim 1, wherein said first and said second data are computed and read-out as a function of input signals, entered into said de-centralized unit.

17. The process of claim 16, wherein said input signals are entered manually.

18. The process of claim 16, wherein after said input signals have been entered, a work piece carrier is first selected within said de-centralized unit, said work piece carrier being then provided with a plastic material blank to be worked and being then fed to a working installation.

19. The process of claim 18, wherein a marking on said work piece carrier is read out and is then linked with said input signals to a set of data.

20. The process of claim 19, wherein said second data read out from said first memory as a function of said input signals are added to said set of data.

21. The process of claim 19, wherein said set of data is transmitted to said central unit and is stored therein.

22. The process of claim 1, wherein said central unit has a second memory in which updates for said second data are stored, wherein, further, prior to reading-out said second data from said second memory, said second data are compared with said updates.

23. The process of claim 22, wherein said second data in said first memory are replaced by said updates if said second data are not in accordance with said updates.

24. An apparatus for making plastic material spectacle lenses, comprising:
 a) a central unit having a computing stage for computing first data for individualized spectacle lenses,
 b) a plurality of de-centralized units connected to said central unit by a line network, said de-centralized units having:
  i) memories for second data for non-individualized spectacle lenses,
  ii) a working installation for working surfaces of plastic material blanks,
  iii) a computer for controlling said working installation as a function of data representing a surface of said spectacle lens when in a finished state as well as parameters of said work process, said computer having means for controlling said working installation either as a function of said first or of said second data.

* * * * *